United States Patent

Cesarczyk

[11] Patent Number: 5,922,614
[45] Date of Patent: Jul. 13, 1999

[54] SAMPLE COLLECTION METHOD WITH EXTRACTION SLEEVE

[75] Inventor: Edward J. Cesarczyk, North Easton, Mass.

[73] Assignee: Avitar Incorporated, Canton, Mass.

[21] Appl. No.: 08/869,105

[22] Filed: Jun. 4, 1997

[51] Int. Cl.⁶ .................................................... G01N 1/02
[52] U.S. Cl. .................... 436/180; 436/174; 436/177; 422/55; 422/56; 422/58; 422/102
[58] Field of Search .................... 422/55, 56, 58, 422/59, 99, 102; 436/174, 177, 180; 604/1, 2; 15/145

[56] References Cited

U.S. PATENT DOCUMENTS

| | | | |
|---|---|---|---|
| 1,687,471 | 10/1928 | Dorman et al. | 604/1 |
| 3,871,375 | 3/1975 | Bennett | 604/1 |
| 4,123,224 | 10/1978 | Givner et al. | 422/59 |
| 4,283,809 | 8/1981 | Prost | 15/145 |
| 4,820,259 | 4/1989 | Stevens | 604/2 |
| 5,000,193 | 3/1991 | Heelis et al. | 128/760 |
| 5,000,202 | 3/1991 | Stepan | 132/320 |
| 5,022,409 | 6/1991 | Goldstein et al. | 128/760 |
| 5,147,288 | 9/1992 | Schiavo | 604/1 |
| 5,260,031 | 11/1993 | Seymour | 422/101 |
| 5,268,148 | 12/1993 | Seymour | 422/101 |
| 5,283,038 | 2/1994 | Seymour | 422/101 |
| 5,339,829 | 8/1994 | Thieme et al. | 128/760 |
| 5,376,337 | 12/1994 | Seymour | 422/101 |
| 5,380,492 | 1/1995 | Seymour | 422/101 |
| 5,393,496 | 2/1995 | Seymour | 422/101 |
| 5,427,739 | 6/1995 | Meserol et al. | 422/58 |
| 5,479,937 | 1/1996 | Thieme et al. | 128/760 |
| 5,494,646 | 2/1996 | Seymour | 422/101 |

*Primary Examiner*—Harold Y. Pyon
*Attorney, Agent, or Firm*—George W. Neuner

[57] ABSTRACT

A method for collecting a sample of fluid specimen from a patient for diagnostic testing, providing a specimen collecting device comprising a hollow tubular member, an elongated foam member that is circumscribed by a hollow tubular member along a portion of its longitudinal axis. The hollow tubular member has a cross sectional area less than the uncompressed cross sectional area of the foam member so that the foam member is compressed along the circumscribed portion. Around the hollow tubular member is slidably mounted a flexible sleeve member having a first end that fits snugly around the hollow tubular member and a second end with an enlarged diameter that can surround the uncompressed foam member.

6 Claims, 1 Drawing Sheet

SAMPLE COLLECTION METHOD WITH EXTRACTION SLEEVE

FIELD OF THE INVENTION

The present invention is related to devices for collection of specimen and delivery of specimen for diagnostic testing, particularly collecting and delivering, e.g., saliva or urine, or the like, for diagnostic tests. The device of the present invention provides an absorbent foam member and a sleeve for extracting the fluid specimen from the member, and is particularly useful for the collection and simple delivery of a specimen from a mammal while maintaining aseptic conditions.

BACKGROUND OF THE INVENTION

Various methods and devices have been used to collect and deliver specimen for diagnostic testing. One conventional method for collecting a saliva specimen is to use a cotton swab. The saliva sample can then be applied to a test device by contact with the swab or the sample can be rinsed from the swab.

Various devices comprising test tube like structures with sample absorbing means have been described for collecting biological samples for diagnostic testing. Examples of such devices are described in U.S. Pat. No. 4,123,224, U.S. Pat. No. 5,000,193, U.S. Pat. No. 5,022,409, U.S. Pat. No. 5,260,031, U.S. Pat. No. 5,268,148, U.S. Pat. No. 5,283,038, U.S. Pat. No. 5,339,829, U.S. Pat. No. 5,376,337, U.S. Pat. No. 5,380,492, U.S. Pat. No. 5,393,496, U.S. Pat. No. 5,479,937 and U.S. Pat. No. 5,494,646.

In a copending application, U.S. Ser. No. 08/712,682, a simple device for collecting and delivering a specimen for diagnostic testing is described. In accord with the disclosure, a specimen collecting device comprises an elongated foam member having a longitudinal axis and an uncompressed cross sectional area, the elongated foam member being circumscribed by a hollow tubular member along a portion of the longitudinal axis, the hollow tubular member has a cross sectional area less than the uncompressed cross sectional area of the foam member so that the foam member is compressed along the circumscribed portion.

SUMMARY OF THE INVENTION

The present invention provides an improved device for collecting and delivering a specimen for diagnostic testing, wherein the device provides a simple and convenient method for extracting the sample from a foam member. In accord with the present invention, a specimen collecting device comprises an elongated foam member having a longitudinal axis and an uncompressed cross sectional area, the elongated foam member being circumscribed by a hollow tubular member along a portion of the longitudinal axis, the hollow tubular member has a cross sectional area less than the uncompressed cross sectional area of the foam member so that the foam member is compressed along the circumscribed portion. Around the hollow tubular member is a flexible sleeve member having a first end that fits snugly around the hollow tubular member and a second end with an enlarged diameter that can surround the uncompressed foam member. Conveniently, the sleeve member can be moved along the hollow tubular member to cover and uncover the portion of the foam member that is not circumscribed by the hollow tubular member.

The sample collection device of the present invention is particularly useful for collecting saliva specimen and delivering the sample to a DNA collection matrix from which DNA for PCR testing can be isolated. The collection device of the present invention provides a simple and inexpensive method for collecting and delivering the saliva sample. Further, in preferred embodiments, the foam member of the collection device provides more consistent and accurate samples.

The sample collection device of the present invention is also particularly useful for collecting saliva or urine specimen and delivering the sample for a rapid drug abuse test.

The collection and delivery device of the present invention provides a simple and inexpensive device for asepticly collecting and delivering a specimen sample. In preferred embodiments of the present invention, the foam member with the flexible sleeve of the collection and delivery device provide more consistent and accurate aseptic samples.

The sample collection devices of the present invention can be used to provide fluid samples, particularly saliva or urine samples, for DNA testing for forensic and paternal identification, RNA testing, antibody testing, testing for particular drugs, and other similar diagnostic procedures.

DETAILED DESCRIPTION OF THE INVENTION INCLUDING PREFERRED EMBODIMENTS

Figure 1:
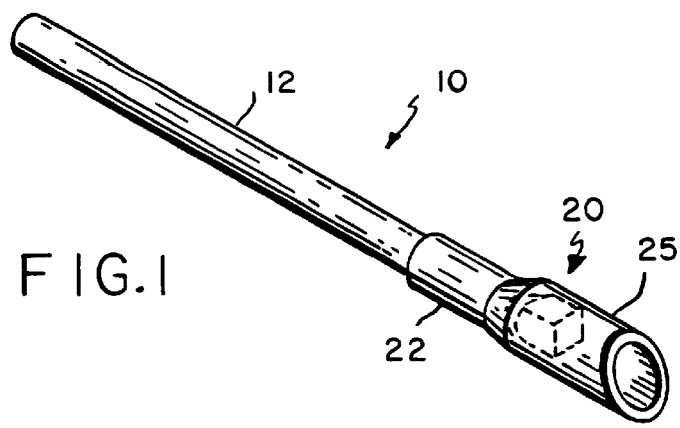
FIG. 1 is an isometric view of a sample collection device in accord with one embodiment of the present invention.
Figure 2:
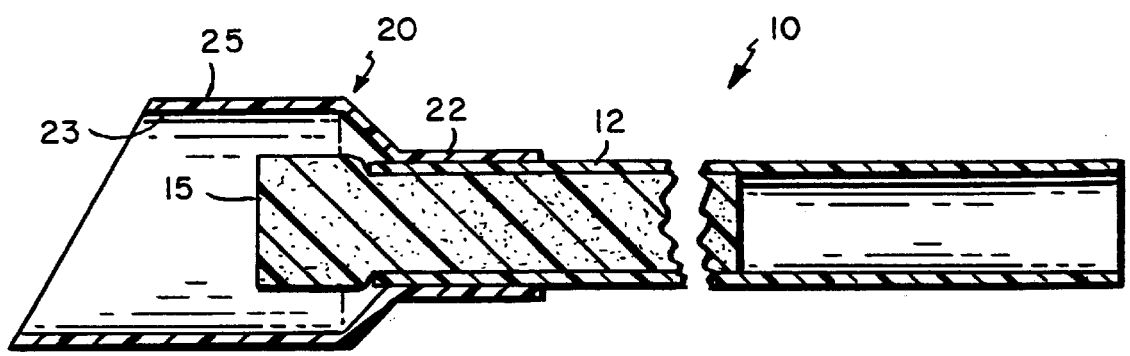
FIG. 2 is a cross sectional view along the longitudinal axis of the sample collection device of FIG. 1, illustrating the sleeve member surrounding the foam member.
Figure 3:
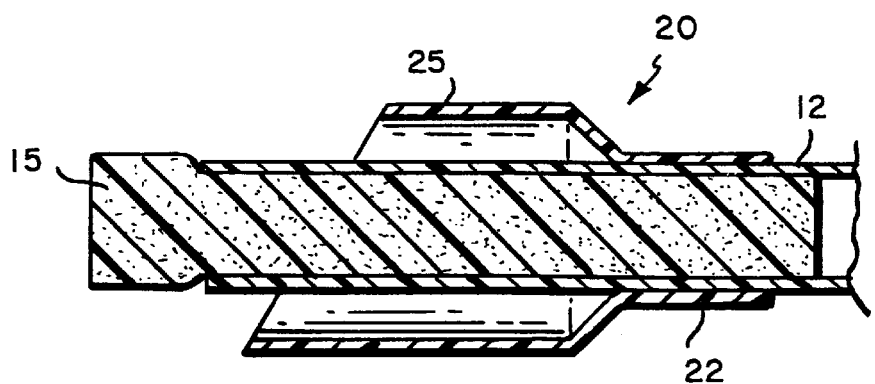
FIG. 3 is a cross sectional view along the longitudinal axis of the sample collection device of FIG. 1, illustrating the sleeve member surrounding the hollow tubular member with the foam member exposed.

The sample collection device in accord with the present invention will be described with reference to the drawings. FIG. 1 illustrates an embodiment of the present invention wherein a sample collection device 10 is made with a hollow tube member 12 containing an elongated piece of foam 15. The foam member 15 is compressed along its longitudinal axis where it is circumscribed by the tube 12. At the end of the sample collection device 10, the foam member 15 protrudes from the tube 12. A flexible sleeve member 20 is provided to cover the foam member and provide a convenient means for extracting the sample from the foam member. The sleeve member 20 is slidably mounted on the tube 12 to uncover the foam member 15 for collecting the sample.

The protruding volume of foam is the primary location for absorption of the sample for delivery for testing. The protruding volume of the foam member is selected depending upon the type of fluid being sampled and the volume of fluid required for the particular diagnostic test. Generally, the foam will protrude from the end of the tube a distance equal to about 25% to about 400% of the mean diameter of tube. If the tube is not circular, the largest dimension of the cross section can be used to approximate the mean diameter for this purpose. Alternatively, the foam will protrude generally a distance of about 0.125 inch to about 2 inches from the end of the tube, depending upon the diameter of the tube. Preferably, the foam protrudes from the tube a distance of one to three times the mean diameter of its uncompressed cross section for saliva collection, and about one to two times the mean diameter for urine collection.

The foam also should extend into the tube for a sufficient distance to be retained in the tube. Generally, the foam should extend into the tube a distance of at least equal to the cross section of the tube. Preferably, the foam should extend into the tube at least equal to the length of the foam protruding from the tube. Of course, the foam can extend the full length of the tube if desired.

The foam member 15 can be made of a variety of absorbent foams. Preferably, the foam is formed and cut to the desired size to expose the cell structure rather than a molded foam part having a surface skin. Preferred materials for the foam member include, for example, polyurethane foam, polyethylene foam, polyvinylchloride foam, ethylvinylacetate foam, polyethylene/ethylvinylacetate foam, polyester foam and polyether foam. Absorbent Porex™, silicone and latex foams can also be used. A particularly useful foam for the collection of saliva is a polyurethane foam sold under the mark HYDRASORB® by Avitar, Inc., Canton, Mass.

The preferred polyurethane foam has a uniform cell count of about 60 or more cells per linear inch. More preferably, the uniform cell count is about 80 to 120 cells per linear inch.

The tube 12 circumscribing the foam can be made of any suitable material having sufficient strength to compress and hold the foam member and to be handled during collecting and delivery of the specimen. Typical materials used for conventional straws, for example, paper tubes and polyethylene, polypropylene, polyester, vinyl or other plastic tubes, are suitable for the tube. Such straws also are economical and an appropriate diameter for, manufacturing of the collection device, handling and use. A circular cross section for the tube is preferred for convenience. However, other shaped cross sections, such as square or triangular tubes, also can be used.

The sleeve 20 has a portion 22 snugly fitted to the tube 12 and a portion 25 with an expanded diameter to cover the foam 15 that is exposed at the end of the tube 12 without touching the foam. Preferably, the sleeve 20 will have the same cross sectional shape as the tube 12, at least at the portion 22 where it snugly fits around the tube. The portion 25 for covering the foam 15 can have any shape that has a volume sufficient to cover and protect the foam 15. Conveniently, the portion 25 of the sleeve has the same cross-sectional shape as the portion 22, only expanded in size. A preferred shape for the sleeve is a funnel shape.

Materials useful for the sleeve 20 can be the same materials useful for the tube 12. For example, paper tubes and polyethylene, polypropylene, polyester, vinyl or other plastic tubes, are suitable for the sleeve. Any material can be used that has sufficient rigidity to maintain a funnel shaped structure to cover the foam member but is flexible enough to permit squeezing the foam member through the sleeve to extract the fluid sample. The material should also be inert to the fluid sample. Those skilled in the art can readily select a suitable material form the wide variety of materials known for medical use and diagnostic testing.

The particular dimensions of the sample collecting device of the invention can vary depending upon the volume of specimen desired and the manner of handling the device for sample collection and delivery. For manual use, it is preferred that the tube length of the device be from about 3.0 inch to about 24.0 inches long and that the mean cross sectional diameter of the tube be from about 0.12 to about 0.5 inch. Although the tube can be longer or shorter, shorter tubes with a sleeve may be difficult to handle and longer tubes require unnecessarily excessive materials.

A particularly useful collection device 10 has a circular hollow tube 12 five (5.0) inches long and 0.22 inch in diameter. An elongated foam member 15 is precut having a length of 3.5 inches and a square cross section 0.25 inch per side. The foam member 15 is compressed and inserted into the tube 12 so that 0.5 inch of foam protrudes from one end. A sleeve, about 2.5 inches long, is provided with one end having about a 0.75 long portion with an inside diameter of about 0.25 inch to fit snugly around the tube. The opposite end of the sleeve has an inside diameter about 0.5 inch with the open end cut on a diagonal. This device can be used to collect a sample. The tube provides a convenient handle to hold the device during use.

To collect a sample, the sleeve is moved longitudinally along the tube to expose the foam member. A fluid sample, e.g., saliva or urine, or the like, can be collected by wicking the fluid into the foam member in as little as 15 seconds by touching the foam member to the fluid. The fluid can be delivered for diagnostic testing by dabbing the foam member onto a slide or membrane, or other device. Alternatively, the sleeve can be moved longitudinally along the tube to cover the foam member and pressure can be exerted on the tube to compress or squeeze the foam and extract the sample from the foam for delivery.

The collection device of the present invention is particularly useful to provide fluid samples extracted from the foam for diagnostic analysis or identification of DNA, RNA, antibodies, drugs, and the like.

The sample collection device of the present invention also is useful for collecting samples of saliva and spotting the samples from the foam onto a matrix device for subsequent isolation of DNA for PCR. Conveniently, the collection matrix is provided in a card form having circular areas outlined for spotting the samples. After collecting the saliva, the foam is dabbed in the circle to spot a sample. After spotting the sample is dried. DNA is isolated from the spotted sample for analysis using a PCR technique (see, for example, Cheng et al., *Proc. Natl. Acad. Sci. USA.* 91:5695–5699 or Wright et al., *J. Clin. Microbiol.* 32: 464–468). The collection matrix can be a conventional paper matrix or, preferably, a collection matrix sold under the brand name IsoCode™ by Schleicher & Schuell, Keene, NH 03431.

The invention has been described in detail with reference to preferred embodiments thereof. However, it will be appreciated that, upon consideration of the present specification and drawings, those skilled in the art may make modifications and improvements within the spirit and scope of this invention as defined by the claims.

I claim:

1. A method for collecting a sample of fluid specimen from a patient for diagnostic testing, the method comprising:

providing a specimen collecting device comprising a hollow tubular member, an elongated foam member having a length along a longitudinal axis and an uncompressed cross sectional area, the elongated foam member being circumscribed by a hollow tubular member along a portion of the longitudinal axis, the hollow tubular member having a cross sectional area less than the uncompressed cross sectional area of the foam member so that the foam member is compressed along the circumscribed portion, and a flexible sleeve member slidably mounted on the hollow tubular member, the flexible sleeve member having a first end that fits snugly around the hollow tubular member and a second end with an enlarged diameter that can surround the uncompressed foam member;

sliding the flexible sleeve member along the hollow tubular member to expose the foam member;

placing one end of the specimen collecting device in a sample of the fluid of the patient to absorb the fluid into the foam member;

removing the specimen collecting device from the sample;

sliding the flexible sleeve member along the hollow tubular member to cover the foam member; and squeezing the foam member through the flexible sleeve member to extract a portion of the fluid absorbed by the foam.

2. The method of claim 1, wherein the foam member of the specimen collecting device has a largest dimension of the cross sectional area and the foam member protrudes from an end of the tubular member a distance of about 25% to about 400% of said largest dimension of the uncompressed cross sectional area of the foam member.

3. The method of claim 1, wherein the foam member protrudes from an end of the tubular member a distance of about 0.125 to about 2 inches.

4. The method of claim 1, wherein the hollow tubular member of the specimen collecting device has a length of from about 3.0 inch to about 24.0 inches.

5. The method of claim 1, wherein the hollow tubular member of the specimen collecting device has a mean diameter of from about 0.12 to about 0.5 inch.

6. The method of claim 1, wherein the foam member of the specimen collecting device comprises a polyurethane foam.

* * * * *